United States Patent [19]

Yamamoto

[11] 4,398,894
[45] Aug. 16, 1983

[54] METHOD FOR QUANTITATIVELY DETERMINING THE DEGREE OF AGGLUTINATION OF PARTICLES

[75] Inventor: Hiroshi Yamamoto, Uji, Japan

[73] Assignee: Kabushiki Kaisha Kyoto Daiichi Kagaku, Kyoto, Japan

[21] Appl. No.: 271,386

[22] Filed: Jun. 8, 1981

[30] Foreign Application Priority Data

Jun. 12, 1980 [JP] Japan .................................. 55-79821

[51] Int. Cl.³ ..................... G01N 33/54; G01N 35/08; G01N 21/85; G01N 21/03
[52] U.S. Cl. ..................................... 436/517; 422/73; 422/82; 436/509; 436/514; 436/524; 436/534; 436/805; 73/64.1
[58] Field of Search .................... 422/73, 82; 436/509, 436/517, 514, 524, 534, 805; 73/64.1

[56] References Cited

U.S. PATENT DOCUMENTS

| | | | |
|---|---|---|---|
| 3,432,268 | 3/1969 | Umger | 422/73 X |
| 3,488,156 | 1/1970 | Good | 422/73 |
| 3,524,366 | 8/1970 | Hrdina | 422/82 X |
| 3,600,953 | 8/1971 | Israeli | 422/82 X |
| 3,679,367 | 7/1972 | Negersmith | 422/82 X |
| 3,699,004 | 10/1972 | Skeggs | 422/82 X |
| 3,814,585 | 6/1974 | Bailly | 422/73 X |
| 3,861,877 | 1/1975 | Matharani | 422/73 X |
| 3,912,452 | 10/1975 | Sodickson | 422/82 X |
| 4,253,846 | 3/1981 | Smythe | 422/82 X |

*Primary Examiner*—Sidney Marantz
*Attorney, Agent, or Firm*—Darby & Darby

[57] ABSTRACT

A method and apparatus for quantitatively determining a degree of agglutination of a suspension of particles or the presence of the agglutination thereof is disclosed, wherein a liquid which contains agglutinated clots, otherwise a substance or substances to be about to agglutinate is made to slowly transfer through a small tube, in course of which agglutinated clots and non-agglutinated particles separate from each other in the liquid, when a degree of agglutination of particles and the concentration of the substance to be tested herewith can be determined quantitatively through the detection of difference in the optical properties of both the accumulation layer of agglutinated clots and the suspension layer of non-agglutinated particles, or the change in the optical properties of either of the above two layers, in particular the suspension layer.

10 Claims, 8 Drawing Figures

METHOD FOR QUANTITATIVELY DETERMINING THE DEGREE OF AGGLUTINATION OF PARTICLES

BACKGROUND OF THE INVENTION

This invention relates to a method and apparatus for quantatively determining a degree of agglutination of particles with the help of optical means and more particularly is concerned with the optical measurement of the state of agglutination of particles while making them agglutinate through the antigen-antibody reaction by using sensitized particles being coated with an emulsion containing either antigen or antibody.

The cognition of the state or existence of the agglutination in a suspension of particles is helpful to grasp the chemical or mechanical properties, stability, and reactivity of it.

In particular, the agglutination reaction—in which sensitized particles such as latex, bentonite, or kaolin being coated with an emulsion containing either antigen or antibody are made to react with the other inversely corresponding antibody or antigen being possibly contained in a liquid to be tested—is being put to practical use as a simple and easy measuring method of immuno-chemical ingredients. Best of all, the agglutination reaction carried on in latex composed of polystyrene and the like is serviceable especially at the time of measuring various sorts of proteins and hormones including RF (rheumatoid factor), CRP (c-reactive protein), and others because of the detecting sensitivity of high grade with an excellent specificity.

For the time being, however, the measurement of the agglutination reaction of such a kind of latex is made as a rule depending on the decision of the presence of the latex which has agglutinated through the antigen-antibody reaction in making the sensitized latex liquid react with the liquid to be tested usually on slide glass or plate, on the basis of eye measurement, otherwise on some occasion by the use of optical means. The results of measurement in both cases mentioned above may be stated as having done throughout in a qualitative way. Especially, in the case of eye measurement, it is ready to cause each time the obscurity in deciding the presence of the agglutination.

Further, in the case of resorting to the optical measuring method, and aiming at the quantitative measurement at that, it is necessary to prepare a series of test objects having been diluted in stages, observe the presence of the agglutination about each sample out of the series while manipulating the reaction, and take a measure to indicate the quantity of antigen or antibody by detecting which stage of dilution forms the boundary layer discriminating the state of agglutination from the state of non-agglutination. Such being the case, the procedure as mentioned above has such a marked imperfection that needs much labor and time or a great deal of latex reagent at the time of measuring even one sample.

On the other hand, there is a way of measuring the light transmissivity of the liquid in the cell by means of a light of wave length belonging to the near infra-red region with the object of quantatively determining a degree of agglutination. In this case, quite a hard point to settle lies in that inasmuch as the clots of agglutinated latex and the other particles of non-agglutinated latex coexist within the observation area of the example, the measurement of the transmissivity, for example, cannot help being done on the mixed system of the clots of agglutinated latex and the particles of non-agglutinated latex, as a result bringing about the drop in its sensitivity. It makes no difference even if some scattered light would be used. This method has another defect that the reproducibity of the measurement done is not good because the agglutinated clots are scattering distributed.

Further, there is also a method for quantitatively determining a degree of agglutination in which the agglutination of latex is made to carry on in a suitable vessel, the agglutinated clots are made separated from the non-agglutinated particles of latex by means of the centrifugal precipitation of the reactant liquid, and then the transmissibity of its supernatant liquid comes to be measured. In this case, however, the provision of a centrifugal separator and a relative operational process are required, all the more the measurement becoming complicated.

In addition to the above, there is still more known a method for detecting the presence of the agglutination through the measurement of the viscosity with regard to common latexes in the field other than the immunochemistry. This method also involves various problems such as the consumption of a comparatively great deal of samples, the intricacy in the temperature control and working curves, and so on, therefore being not able to expect the exactitude of the measurement.

SUMMARY OF THE INVENTION

It is an object of this invention is to eliminate the above-mentioned defects and provide a method for quantitatively determining a degree of agglutination of a suspension of latex, or, more generally, common particles with the objective reproducibility of the agglutination reaction or the state of agglutination thereof. Another object of this invention is to provide a method by which the measurement can be performed automatically, and an apparatus which is materialized in a simple construction for applying the same with ease. A further object of this invention is to provide a method for quantitatively measuring the immunochemical ingredients on the basis of the antigen-antibody reaction, and an apparatus on which the above measurement is to be performed automatically and continuously.

These objects of the invention will be achieved by observing and measuring the difference in the optical properties between the both layers of the suspension or the change in optical properties of either layer thereof which has been separated into agglutinated clots and non-agglutinated particles while the suspension is made to transfer slowly through a small tube by taking advantage of the transfer characteristic of the suspension flowing through the small tube.

The other objects than the above will become obvious from a reading the description in detail given hereinafter.

DETAILED DESCRIPTION

Description will be now directed to the details of the invention with reference to the accompanying drawings while taking the case of adding a test sample, which contains antibody or antigen as a substance to be tested, to a sensitized latex which is used as a suspension of particles. Incidentally, the case mentioned above implies that the suspension of particles is used in the capacity of reagent. Contrary to this, it is also possible to detect the substance to be tested which is contained in the suspension of particles by the use of a different kind of reagent. The example of the latter case, however, was omitted in the following for the simplification of explanation.

The flow velocity of the fluid flowing through a small tube is more rapid in the vicinity of the center of the section, and becomes slower the more it nears toward the wall of the tube, under the influence of the viscosity and the friction between the tube wall and the fluid. It is known that when the flow velocity is small and the laminar flow is formed, the distribution of the flow velocity within a circular straight tube takes a form of parabola, as shown in FIG. 1, wherein let the radius of the tube be "a" and the maximum flow velocity be $V_M$, then the flow velocity V at the spot remote from the center of the tube by a distance r is equal to $V_M(1-r^2/a^2)$, and the average flow velocity $\overline{V}$ is equal to $\frac{1}{2}V_M$.

Figure 1:
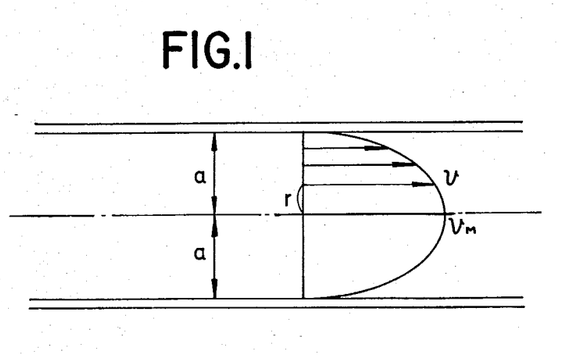
FIG. 1 is a typical diagram of the velocity distribution of a fluid flowing through the duct of a small tube.
Figure 2:
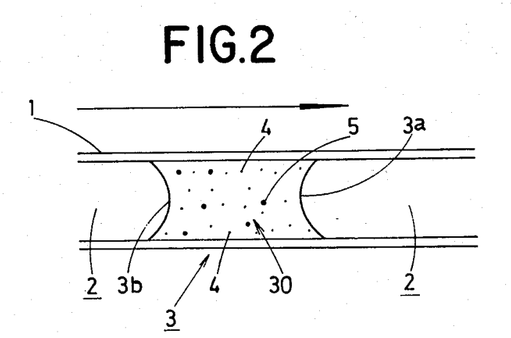
FIG. 2 is an enlarged sectional view showing the state of a vacuole in the small tube.

Now, when a latex reagent which is sensitized with antigen or antibody is allowed to react with a test sample containing antibody or antigen in the interior of a reaction vessel, a prescribed quantity of the reactant liquid (30) thus created is sucked into a small tube (1), as shown in FIG. 2, being sandwiched in between the front and rear air layers (2), and the vacuole (3) of the reactant liquid (30) is made to transfer at a low speed in the direction of the arrow, then the distribution of the flow velocity of the reactant in the central part of the vacuole (3) becomes approximately as shown in FIG. 1, when the vacuole has a more rapid speed the more it nears toward the central part. However, there are generated vortexes at the front and rear of the vacuole (3) contacting with the air layers (2), so that the liquid close to the tube wall is caught up into the central part at the meniscus part (3b) of the rear, thereby moving on forward at a speed more than the average flow velocity.

When the sensitized latex particles (4) will not agglutinate, then those particles transfer for the most part along the liquid current in the direction of the arrow, the particles which have moved on toward the front part of the vacuole (3) are caught up into the vortexes at the front meniscus part (3a) to shift to the side of the tube wall, and after that turn relatively backward. Consequently, the state of suspension becomes uniform almost throughout the whole vacuole, and present the behavior as if the reactant liquid were transferring while being merely mixed by stirring.

Figure 3A:
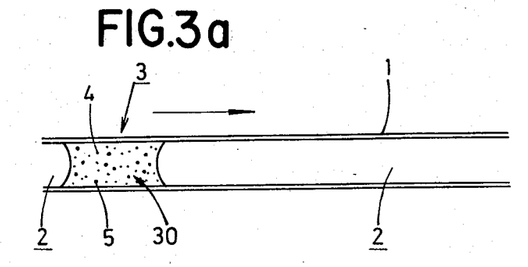
FIG. 3 is an enlarged sectional view showing the state of a vacuole flowing through the small tube as well, in which (a), (b), and (c) indicate the initial state of transfer, the interim state where many agglutinated clots are gathering at the front part of the vacuole, and the state where those agglutinated clots have accumulated at the front part, when the whole vacuole has divided into two layers: an accumulation layer of agglutinated clots and a suspension layer of non-agglutinated latex particles, respectively.
Figure 3B:
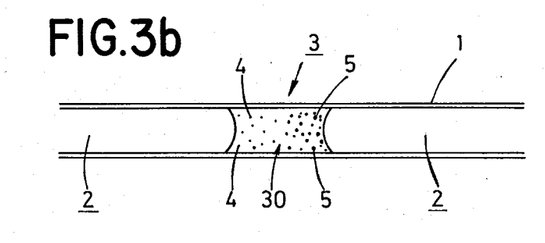
Figure 3C:
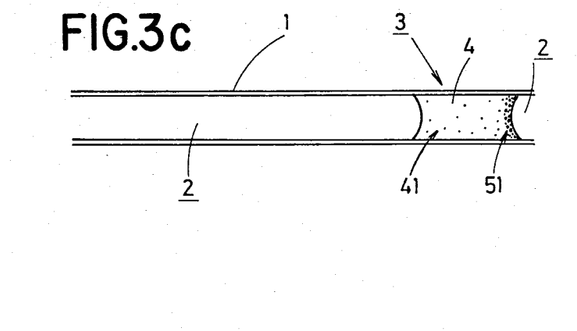

On the contrary, when the agglutination reaction proceeds and a good many agglutinated clots (5) . . . come to grow, then several phenomena distinct from the above are perceived as follows:

When the reactant liquid (30) in which the agglutinated clots (5) are growing, or the reactant liquid (30) which contains the agglutinated clots (5) from the beginning, is made to be sucked into the small tube (1) and subsequently to move on slowly forward (FIG. 3(a)), then the reactant liquid (30) in the vacuole (3) transfers while being stirred similarly to the case of FIG. 2, but the distribution of the agglutinated clots (5) . . . will not become uniform, and it is perceived that the agglutinated clots (5) . . . go to concentrate and accumulate on the front part of the vacuole (3), as shown in FIG. 3(b) and (c). This is for the reason that the agglutinated clots (5) of latex entwine each other easily to agglutinate, wherein the agglutinated clots (5) . . . which have ridden on the rapid flow in the center of the small tube (1) collide while rotating with the other agglutinated clots (5) . . . on the way, grow to the larger agglutinated clots, and finally reach the front part of the vacuole (3) (FIG. 3(b)). The agglutinated clots (5) . . . having reached the front part of the vacuole (3) come to accumulate thereat while losing their rapid speed without being caught up into the vortexes at the meniscus part (3a) of the front because of their largeness in sige and agglutinativeness. Against and to these agglutinated and accumulated clots strike and adhere the newly following agglutinated clots from behind to form a larger aggregate of agglutinated clots at the front part (FIG. 3(c)).

If the vacuole (3) is made to transfer in a state of having extended the length of the small tube (1) so as to take more hours in its shifting movement, the agglutinated clots (5) . . . come to gather consecutively at the front part. In the interim state until the complete separation, the concentration gradient of the agglutinated clots (5) . . . is already generated along the progressive direction of the vacuole (3), where the concentration is higher the more it lies near the front part of the vacuole (FIG. 3(b)), finally the reactant liquid coming to be separated into two layers (FIG. 3(c)). The front layer is an aggregate or an accumulation layer (51) of agglutinated clots (5) . . . . The rear layer is a suspension layer (41) of non-agglutinated particles (4) of latex. With the lapse of a proper time of agglutination, the accumulation layer (51) of agglutinated clots in the front becomes thicker and thicker as the agglutination reaction proceeds with the increasingly high degree of agglutination, in proportion to which a large number of latex particles (4) is consumed for it. Consequently, in the rear, the suspension layer (41) composed of non-agglutinated particles (4) of latex lowers its concentration correspondingly.

This invention aims at optically measuring the concentration of the reactant liquid (30) in the vacuole (3) composed of both the accumulation layer (51) of agglutinated clots and the suspension layer (41) of non-agglutinated particles of latex, and subsequently quantitatively determining a degree of agglutination at the time of the agglutination reaction of latex through the observation of the behavior of the change in the concentration to be obtained in the foregoing procedure.

Referring further to an embodiment of this invention, the quantitative determination of a degree of agglutination is performed also here by optically measuring the concentration of the suspension layer (41) in the rear part of the vacuole.

In the above case, although the vacuole (3) was sandwiched in between the air layer (2). (2) from both front and rear sides, respectively, it is permissible to use instead of air some other fluid not mingling with the reactant liquid, for example, such as this and that inert gases, silicone, and the like. As for the reactant liquid (30) to be introduced into the small tube (1), it may be the one as of being prepared in advance by mingling the latex reagent with the tests object, as mentioned above, or else it will do if the latex reagent and the test object are fed separately into the small tube to mix each other therein, and are made to react with each other while being transferred.

Figure 4:
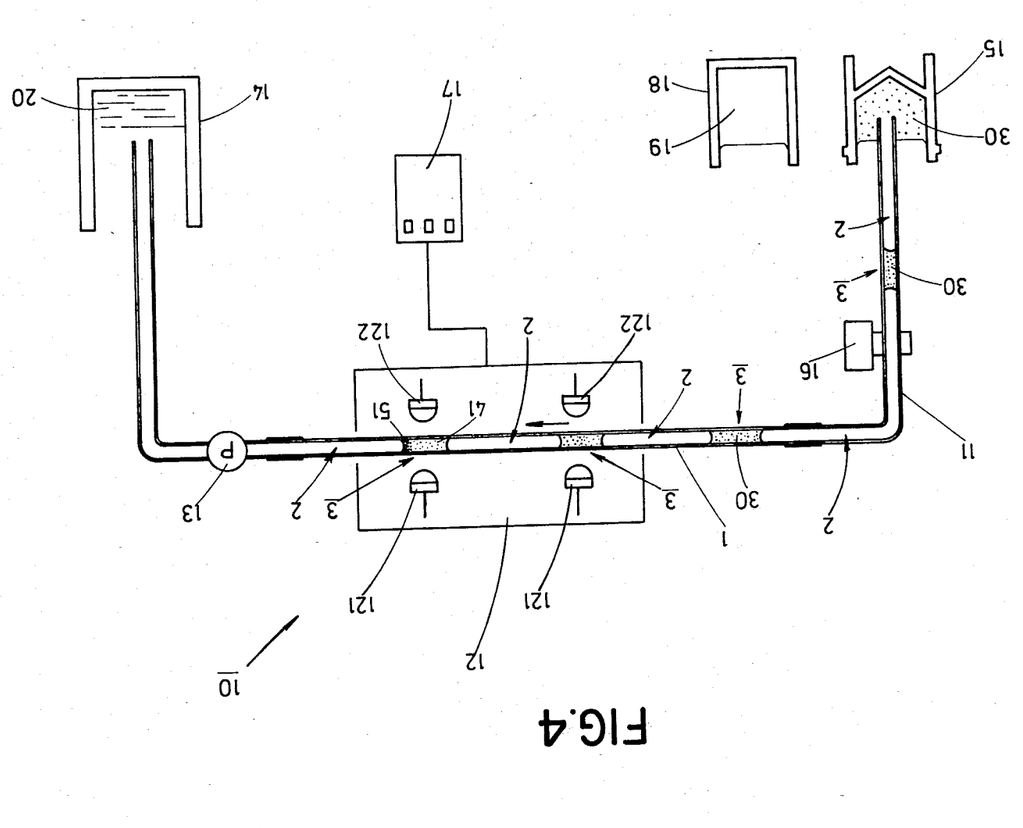
FIG. 4 is a schematic drawing showing an example of the apparatuses according to the present invention.

FIG. 4 shows a schematic drawing of an apparatus for quantitatively determining a degree of agglutination by means of the above-described method. This apparatus (10) comprises a suction nozzle (11), a small tube (1) being connected to the nozzle (11), an optical measuring means (12) being provided on the side part of the small tube (1), a pump (13) sucking a fluid into the small tube (1), and a waste fluid receptacle (14).

As a start, when a fixed quantity of the reactant liquid (30) in a reaction vessel (15) is sucked by the sucking action of the pump (13) throught the nozzle (11), then the nozzle (11) is lifted up out of the reactant liquid by a nozzle-driving device (16), and subsequently it sucks up the air.

In this case, it is a matter of course that some inert gas or silicone can be sucked in place of air. The reactant liquid (30) forms a vacuole (3) being sandwiched in between air layers (2). (2) from behind and before in the interior of the small tube (1) being connected to the nozzle (11), it is moved on slowly in the direction of the arrow by the sucking action of the pump (13), and it reaches the optical measuring means (12) being provided on a part of the system of the small tube (1). This optical measuring means (12) comprises a light source (121) and a light detector (122) for measuring the transmitted light. During the intervening time, the agglutination reaction of the reactant liquid (30) in the vacuole (3) is proceeding (or it does not matter if the reaction might be brought to completion in a sample container). The agglutinated clots (5) accumulate at the front part of the vacuole (3), as shown in FIG. 3, on the back of which the non-agglutinated particles (4) of latex become suspended in the rear reactant liquid. As described above, the reactant liquid (30) in the vacuole (3) shifts while being stirred, so that the non-agglutinated particles (4) of latex in the rear suspension layer (41) are distributed almost uniformly, the concentration of which corresponds to the degree of agglutination of the agglutinated clots of latex. The optical measuring means (12) is for use in measuring the concentration of the reactant liquid consisting of the accumulation layer (51) and the suspension layer (41).

In this connection, when different kinds of reactant liquids (30) . . . are made to be sucked up successively for the purpose of enhancing the efficiency of measurement, it is preferable to dip the nozzle (11) in a wash bowl (18) to such wash liquid (19) in order to prevent the contamination every time of sampling, whereby one to several pieces of vacuoles (not shown) are able to be fed into the small tube (1). In the figure, reference number (20) indicates a waste liquid.

Figure 5A:
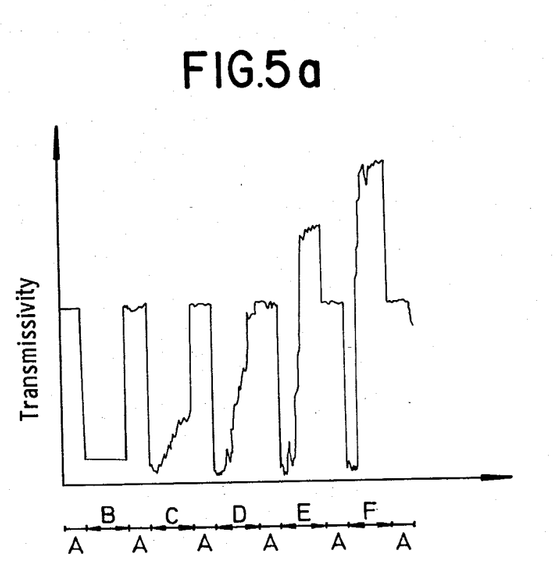
FIG. 5(a) shows a graph being expressive of the respective transmissivities at each step of the transferring vacuole, and FIG. 5(b) indicates the transmissivity of the reactant liquid of a low degree of agglutination in the completely halved state of the vacuole.

When the shifting vacuole (3) is observed by the optical measuring means (12) with the aid of transmitted light, then the curves as seen in FIG. 5(a) are obtained, whereat Steps A . . . denote the transmissivities of the respective air layers (2) . . . , and Steps B to F indicate the transmissivities of the reactant liquid in the vacuole temporally passing the respective steps.

Out of Steps B to F, the first Steps B shows the transmissivity in the case where the reactant liquid did not or does not yet begin the reaction of agglutination, that is, in the case where the particles of latex is not at all consumed for the reaction of agglutination. This transmissivity is uniform trough the whole vacuole. In Step C, the reaction of agglutination is proceeding to some extent, and the accumulation of the agglutinated clots (5) is perceived faintly at the front part of the vacuole, where the transmissivity starts to lower little by little, while on the other hand the transmissivity of the rear suspension layer is rising in some measure (Corresponding to FIG. 3(a)). Step D shows an sample in which the reaction of agglutination is in an advanced stage, and where the accumulated layer (51) of agglutinated clots in the front is increasing more and more, while the transmissivity of the suspension layer (41) in the rear is arriving near to that of the air layer (2) (Corresponding to FIG. 3(b)). Steps E and F show separately the transmissivities of the reactant liquid having displayed the reaction of agglutination stronger than in the former step. In each of these latter two steps, with the increasingly advanced accumulation of agglutinated clots in the front part is exhibited the transmissivity of the suspension layer (41) in the rear to be of the higher value than that of the air layer (2) (Corresponding to FIG. 3(c)).

Figure 5B:
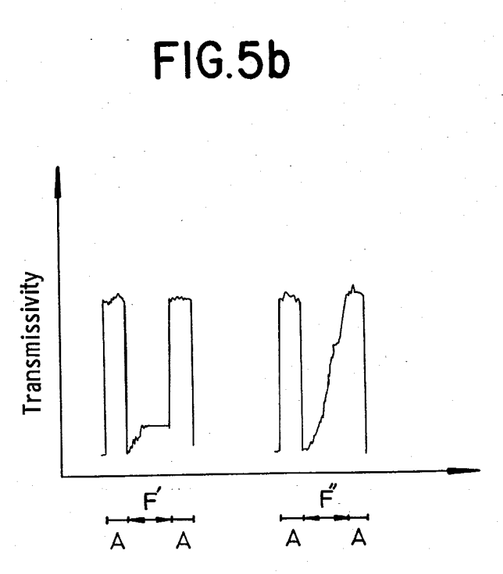
Figure 6:
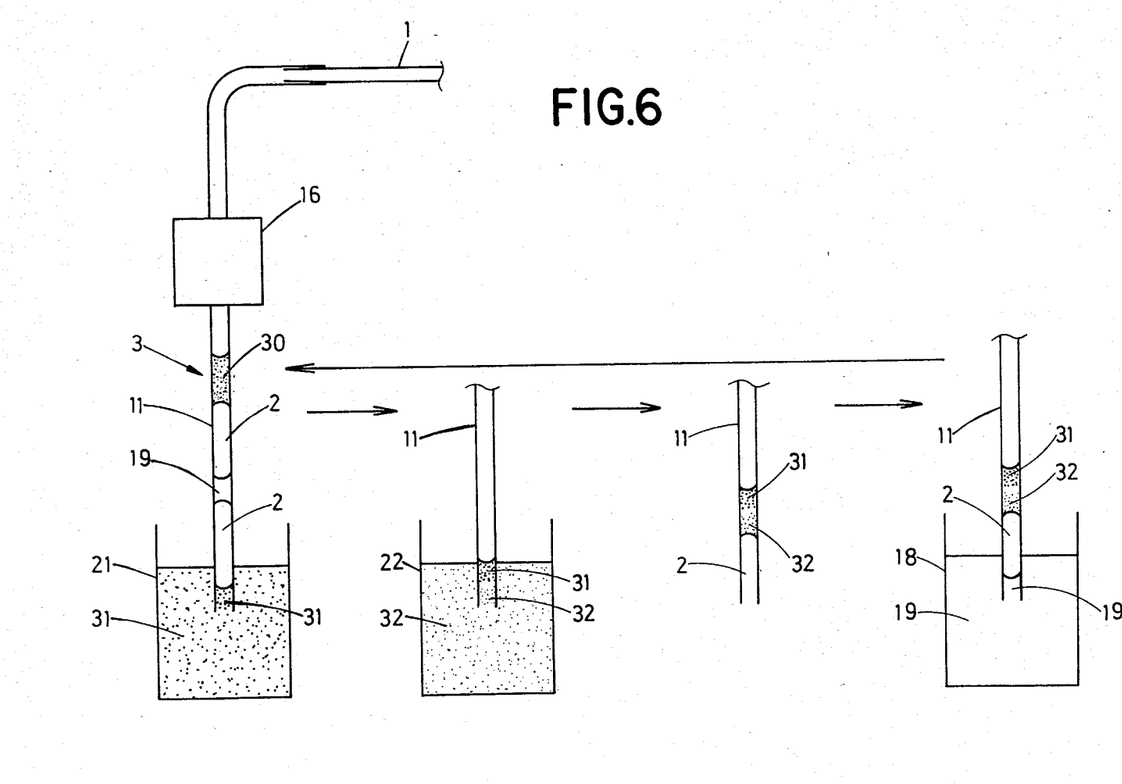
FIGS. 6 and 7 show schematic drawings giving two different examples of the modification of the sample-supplying section of the apparatus according to the invention.

Further, Steps F' and F" shown in FIG. 5(b) each give the transmissivities in the cases where the reactant liquid of the lower degree of agglutination is completely divided in two parts, as compared with the case of F in FIG. 5(a).

Now, seeing from the graphs shown in FIG. 5(a) and (b), it is thinkable that there may be a variety of methods serviceable for the purpose of obtaining a degree of agglutination of the reactant liquid through the utilization of the transmitted light as follows:

To begin with, for example, after the lapse of time sufficient to completely divide the reactant liquid in the vacuole into two layers: The accumulation layer (51) of agglutinated clots and the suspension layer (41) of non-agglutinated particles (Step F in FIG. 5(a), and Steps F' and F" in FIG. 5(b)), the output pattern, otherwise the transmissivity of either of the accumulation layer (51) of agglutinated clots and the suspension layer (41) of non-agglutinated particles is made indicated in a displaying device (17) shown in FIG. 4. If adopting the output pattern, it is possible to judge not only the unevenness of the graph but also the length of duration (time) of the state in question.

On the other hand, if with the invention of using the transmissivity, it is commendable in the present example to take advantage of the transmissivities on the side of the suspension layer (41) because the values of the transmissivities of the accumulation layer of agglutinated clots make little difference among themselves, therefore the resolving power here being bad. On the displaying device (17), however, it is also possible to indicate the degree of agglutination into which the transmissivity has been converted.

Besides the above, it is also conceivably possible that there may be a different method by which the measurement can be made even within a certain period of reaction time after the sample starts to react, but not until the reactant liquid is completely divided into two layers. In this case, it is possible to find a degree of agglutination kinetically also on the basis of the observation of the behavior of the change in a plurality of transmissivities of the suspension layer (41) measured at regular intervals of time, what by arranging the optical measuring means (12) in sets of more than one pair of light source (121) and light sensor (122) (the case of FIG. 4), or what by making the light source (121) and the light sensor (122) move along the small tube (1). Such a measure of pluralization or mobilization of the light source (121) and light sensor (122) can be applied to the case where the measurement will be performed in the complete division of the reactant liquid into two layers.

The above description is concerned with the case where the reactant liquid (30) prepared beforehand is introduced as it is into the small tube (1). However, it is also permissible to supply the latex reagent (31) constituting the reactant liquid (30) and the test object (32) containing antibody or antigen separately into the small tube (1), to make the both mix with each other therein, and further to cause the mixture to react while shifting therethrough. In this occasion, there are sucked through the nozzle (11) successively the latex reagent (31) (latex particles being made sensitized with antigen or antibody) in a reagent vessel (21), the test sample (32) (liquid to be tested possibly containing antibody or antigen) in a test sample container (22), and the wash liquid (19) in the wash bowl (18). At this time, however, it must be mindful so as not to suck the air between the latex reagent (31) and the test sample (32), but so as to suck a sufficient amount of the air in order that a suitable air layer is formed between the above both and the wash liquid (19). By doing so, the reagent (31) and the test sample (32) mix with each other progressively in the upper part of the nozzle (11) and subsequently in the small tube (1) connected thereto, going to the form of a vacuole (3) of the reactant liquid (30).

In the following, the same action to be repeated on exchanging a new test sample for the old one on each occasion will enable the continuous measurement of a number of test samples.

Figure 7:
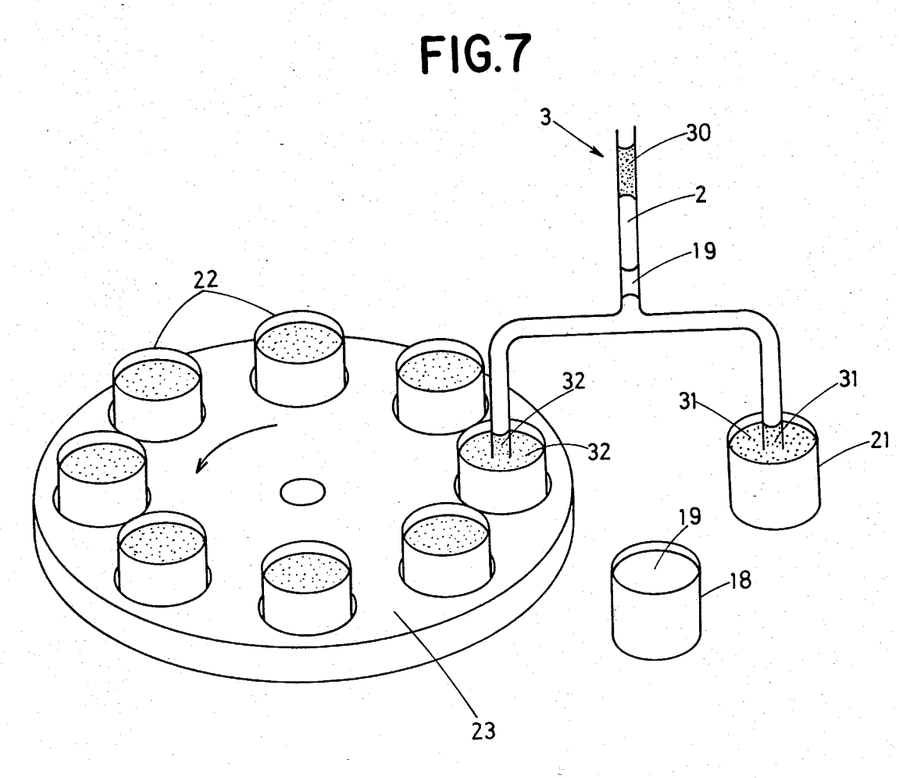

FIG. 7 shows also an example where a branch pipe having two suction ports is used in the stead of the suction nozzle (11). In this case, the latex reagent (31) and the test object (32) are separately sucked and then flow together on the way to form the reactant liquid (30). To remark in passing, arrangement is to be made for the washing of the suction nozzle (11) so as to be able to be done only on the side of the test sample, or else, if necessary, on both sides of the agent and the test sample at the same time. It need scarcely be said that if a plurality of test sample containers (22) are mounted on an intermittently rotating sample stand (23), it becomes possible to automatically measure a number of test samples continuously.

In this way, if the latex reagent (31) and the test sample (32) are gotten ready to be sucked separately in a non-miscible state, it is feasible to save the trouble of mixing and stirring them in advance of sucking, and further to fix the time which is taken after the mixing of the reagent and the test sample at the confluence point until the beginning of the measurement whereby temporal change in the state of agglutination should be advantageously grasped with ease. What is more, if adopting such a design as shown in FIG. 7 capable of performing the automatic and continuous sucking action, it is also possible to promote a splendid labor-saving, without the necessity of constantly attending thereupon.

In all of the above-mentioned examples, it was so devised that the transmissivity may be measured in the state where the vacuole (3) is slowly shifting through the small tube (1) as it is, but it will do if the transmissivity only of the suspension layer (41) is so made as to be measured stopping the stream for a while at the time of the measurement. On the other hand, in the case of the optical measuring means (12) being provided apart from the small tube (1), it will be also at liberty to remove the small tube (1) after the stoppage of the stream, mount it on the above means, and then submit it to the measurement.

In the above examples, although description has been made as regards the cases of applying the transmissivities, it goes without saying that the measurement is able to be carried out also by employing the scattered light or the reflected light. As for the small tube (1) for use in this invention, it is general a typically cylindrical object, and yet the cross-section of it is not always limited to a circle but it can take other forms such as an oval, a square or the others. It is further allowable to use not only a straight pipe but also a coil-like one being wound so as to exhibit somewhat a stirring effect.

The description heretofore was concerned with the agglutination reaction of the latex particles being made sensitized with antigen or antibody. It is to be construed, however, that our invention can be applied extensively beyond the above scope to various cases, for example, such as a case where some mechanical or physical action is added to the suspension of common particles, a case where different kinds of reagents or substance to be tested are added thereto in order to measure the reactivity, the stability or the others, and so on.

As described above, this invention is such a one as to divide a suspension or reactant liquid of particles into two parts: an accumulation layer of agglutinated clots and a suspension layer of non-agglutinated particles while making it slowly shift through a small tube, to optically measure the concentration of the reactant liquid consisting of the accumulation layer of agglutinated clots and the suspension layer of non-agglutinated particles, and thereby to determine a degree of agglutination of particles, in the process of which the measurement can be performed quantitatively with an excellent objective reproducibility.

With the above arrangement, our invention need not dilute one and the same sample in stages each time and does not require any complicated operation such as the centrifugal separation and others, as a result of which it makes possible to continuously measure a great number of samples and that at the same time to settle such kinds of problems as the lowering in the measurement sensitivity and the badness in the reproducibility as are generated at the time of the measurement being conducted in a mixed state of the agglutinated clots with the non-agglutinated particles, whereby the immunochemical ingredients can be measured with simplicity and exactitude through the observation of the agglutination reaction of sensitized latex.

I claim:

1. A method for quantitatively determining the degree of agglutination of particles, which comprises the steps of:

causing a liquid containing the particles to be agglutinated to slowly transfer through a small tube in the form of a vacuole within a fluid immiscible with said liquid;

allowing the particles in said liquid to agglutinate and to accumulate as agglutinated clots on the front part of said vacuole, thereby to form within said vacuole an accumulation layer of said agglutinated clots and a suspension layer of non-agglutinated particles; and measuring the degree of agglutination within said liquid by the use of optical means after the lapse of a predetermined time.

2. A method for quantitatively determining the degree of agglutination of particles as set forth in claim 1, wherein said liquid is a reactant liquid being composed of a suspension of particles and a substance to agglutinate together with said particles.

3. A method for quantitatively determining the degree of agglutination of particles as set forth in claim 1, comprising the steps of successively introducing a plurality of said vacuoles into said small tube by being sucked up by means of a suction nozzle, and being made to move on forward through said small tube to permit the particles to mingle with each other during the movement.

4. A method for quantitatively determining the degree of agglutination of particles as set forth in any one of claims 1, 2 or 3, wherein the concentration of nonagglutinated particles in said liquid other than a portion of the agglutinated clots having accumulated within the vacuole is measured by the use of optical means.

5. A method for quantitatively determining the degree of agglutination of particles as set forth in any of claims 1, 2, or 3, wherein said particles are sensitized with a coating of an emulsion containing one of an antigen and antibody.

6. A method for quantitatively determining the degree of agglutination of particles as set forth in claim 5, wherein latex particles are used in the capacity of carriers of sensitized particles.

7. A method for quantitatively determining the degree of agglutination of particles as set forth in claims 1, 2 or 3, wherein one of air, inert gas and silicone is used in the capacity of said immiscible fluid.

8. A method for quantitatively determining the degree of agglutination of particles as set forth in any of claims 1, 2 or 3, wherein when the degree of agglutination within the respective vacuoles of reactant liquids is to be continuously determined, then a vacuole of a wash fluid is fed in between said vacuoles of reactant liquid.

9. A method for quantitatively determining the degree of agglutination of particles as set forth in claim 8, wherein the steps of separating the reactant liquid within the small tube by vacuoles of wash fluid, and measuring the respective optical properties of the layers being divided into two within each vacuole of the reactant liquid, are performed independently of each other.

10. The method of claim 8 in which the wash fluid comprises an inert gas.

* * * * *